(12) United States Patent
O'Neill et al.

(10) Patent No.: US 8,731,971 B1
(45) Date of Patent: May 20, 2014

(54) COMPUTER-IMPLEMENTED METHODS AND COMPUTER SYSTEMS FOR MASTER DATA MANAGEMENT LEVERAGING A NON-RELATIONAL DATABASES FOR DYNAMICALLY AGGREGATING DATA OF DISTINCT FORMATS AND/OR CONTENT

(71) Applicants: Brian O'Neill, Pottstown, PA (US); Isaac Rieksts, Coopersburg, PA (US); Shantha Andrews, Lansdale, PA (US); P. Taylor Goetz, West Chester, PA (US); Alan Horton, Phoenixville, PA (US)

(72) Inventors: Brian O'Neill, Pottstown, PA (US); Isaac Rieksts, Coopersburg, PA (US); Shantha Andrews, Lansdale, PA (US); P. Taylor Goetz, West Chester, PA (US); Alan Horton, Phoenixville, PA (US)

(73) Assignee: Health Market Science, King of Prussia, PA (US)

( * ) Notice: Subject to any disclaimer, the term of this patent is extended or adjusted under 35 U.S.C. 154(b) by 0 days.

(21) Appl. No.: 14/015,037

(22) Filed: Aug. 30, 2013

Related U.S. Application Data

(60) Provisional application No. 61/798,744, filed on Mar. 15, 2013.

(51) Int. Cl.
*G06F 19/00* (2011.01)
(52) U.S. Cl.
USPC ............................................................ 705/3
(58) Field of Classification Search
USPC ........................................................ 705/2, 3
See application file for complete search history.

(56) References Cited

PUBLICATIONS

Hadoop Overview—www.revelytix.com.Retrieved on Jan. 6, 2014 <<http://www.revelytix.com/?q=content/hadoop-overview>>.
Hadoop—Overview; Enterprise IT Slideshow dated Jan. 12, 2009. Retrieved on Jan. 6, 2014 <<http://www.slideshare.net/thecapacity/hadoop-overview-presentation>>.
Bhandarkar, "Hadoop Overview & Architecture"; EMC Academic Alliance Slideshow dated Apr. 4, 2013 Retrieved on Jan. 6, 2014 <<http://www.slideshare.net/emcacademics/milind-hadoop-trainingbrazil>>.
Jones, "Process real-time big data with Twitter Storm: An introduction to streaming big data"; IBM, developerWorks, Technical topics, Open source, Technical Library; Apr. 2, 2013 Retrieved on Jan. 6, 2014 <<http://www.ibm.com/developerworks/opensource/library/os-twitterstorm/index.html?ca=dat>>.
Rationale—nathanmarz/storm Wiki—GitHub Retrieved on Jan. 6, 2014 <<https://github.com/nathanmarz/storm/wiki/Rationale>>.
Tutorial—nathanmarz/storm—GitHub Retrieved on Jan. 6, 2014 <<https://github.com/nathanmarz/storm/wiki/Tutorial>>.

(Continued)

*Primary Examiner* — John Pauls
(74) *Attorney, Agent, or Firm* — Greenberg Traurig, LLP

(57) ABSTRACT

In some embodiments, the instant invention provides for a computer-implemented method that includes steps of: receiving data feeds associated with healthcare-related entities, where a data schema of each data feed is unknown prior to the receipt; automatically determining, in real-time, for each entity, at least: a first type data fragment identifying an identifier associated with the entity and ii) second type data fragments containing items of information about the entity; automatically storing the entity information across distributed non-relational computer databases, by: creating, each time, records, where each record includes a row with columns, where the row is associated with the first identifier and where each column of the row has: 1) a name composed of a hierarchical path to a content of each column and 2) the item of information of the second type data fragment; and determining a verified record of the entity at a particular time.

22 Claims, 10 Drawing Sheets

| 1 [$t_5$] | |
|---|---|
| First_Name | Collin |
| Last_Name | Kelley |
| Phone | ["610-555-7777", "576-555-0123"] |
| License_Number | LP275 |
| Status | Valid |
| Timestamp | $t_5$ |

(56) References Cited

PUBLICATIONS

Graph database; Wikipedia, the free encyclopedia Retrieved on Jan. 6, 2014 <<http://en.wikipedia.org/wiki/Graph_database>>.

Rodriguez, "Putting and Getting Data from a Database" Supporting the Emerging Graph Landscape; Apr. 30, 2011 Retrieved on Jan. 6, 2014 <<http://markorodriguez.com/2011/04/30/putting-and-getting-data-from-a-database/>>.

Property Graph Model—tinkerpop/blueprints Wiki—GitHub Retrieved on Jan. 6, 2014 <<https://github.com/tinkerpop/blueprints/wiki/Property-Graph-Model>>.

Cassandra Essentials Tutorials: Overview of Apache Casandra; DataStax; Resources Retrieved on Jan. 6, 2014 <<http://www.datastax.com/resources/tutorials/cassandra-overview>>.

Goebel, "A Quick Introduction to Apache Cassandra", sitepoint; Programming; Jan. 30, 2013 Retrieved on Jan. 6, 2014 <<http://www.sitepoint.com/a-quick-introduction-to-apache-cassandra/>>.

| PRACT.tab | | |
|---|---|---|
| ID | First Name | Last Name |
| 1 | Owen | Smith |
| 2 | Collin | Kelley |
| 3 | Lisa | Bullard |

| PHONE.tab | | |
|---|---|---|
| ID | PHONE_ID | Phone |
| 1 | 201 | 215-555-3444 |
| 2 | 202 | 610-555-7197 |
| 2 | 203 | 484-555-9823 |

| STATE_LICENSE.tab | | | |
|---|---|---|---|
| ID | LICENSE_ID | License Number | Status |
| 1 | 501 | JK175 | Expired |
| 2 | 502 | LP275 | Valid |
| 3 | 503 | SN112 | Valid |

*Fig. 1*

| 1 [t₀] | |
|---|---|
| PRACT[1] | { First_Name: Owen, Last_Name: Smith } |
| PRACT.PHONE[1.201] | { Phone: 215-555-3444 } |
| PRACT.STATE_LICENSE[1.501] | { License_Number : JK175, Status: Expired } |
| 2 [t₀] | |
| PRACT[2] | { First_Name: Collin, Last_Name: Kelley } |
| PRACT.PHONE[2.202] | { Phone: 610-555-7197 } |
| PRACT.PHONE[2.203] | { Phone: 484-555-9823} |
| PRACT.STATE_LICENSE[2.502] | { License_Number : LP275, Status: Valid } |
| 3 [t₀] | |
| PRACT[3] | { First_Name: Lisa, Last_Name: Bullard } |
| PRACT.STATE_LICENSE[1.501] | { License_Number : JK175, Status: Expired } |

*Fig. 2*

| PHONE.tab (at t₅) | | | |
|---|---|---|---|
| ID | PHONE_ID | Phone | OPERATION |
| 2 | 202 | 610-555-7777 | UPDATE |
| 2 | 203 | 484-555-9823 | DELETE |
| 2 | 299 | 576-555-0123 | UPDATE |

| PHONE.tab (at t₇) | | | |
|---|---|---|---|
| ID | PHONE_ID | Phone | OPERATION |
| 2 | 299 | 576-555-4444 | UPDATE |

*Fig. 3*

| ADDRESS.tab (at t₈) | | | |
|---|---|---|---|
| ID | ADDR_ID | City | State |
| 2 | 700 | Springfield | PA |

*Fig. 4*

| 2 [t₀] | |
|---|---|
| PRACT[2] | { First_Name: Collin, Last_Name: Kelley } |
| PRACT.PHONE[2.202] | { Phone: 610-555-7197 } |
| PRACT.PHONE[2.203] | { Phone: 484-555-9823} |
| PRACT.STATE_LICENSE[2.502] | { License_Number : LP275, Status: Valid } |
| 2 [t₁] | |
| PRACT[2] | { First_Name: Collin, Last_Name: Kelley } |
| PRACT.PHONE[2.202] | { Phone: 610-555-7777 } |
| PRACT.PHONE[2.299] | { Phone: 576-555-0123} |
| PRACT.STATE_LICENSE[2.502] | { License_Number : LP275, Status: Valid } |
| 2 [t₂] | |
| PRACT[2] | { First_Name: Collin, Last_Name: Kelley } |
| PRACT.PHONE[2.202] | { Phone: 610-555-7777 } |
| PRACT.PHONE[2.299] | { Phone: 576-555-4444 } |
| PRACT.STATE_LICENSE[2.502] | { License_Number : LP275, Status: Valid } |

*Fig. 5*

| 1_$t_0$ | |
|---|---|
| SYSTEM.BASIS | -1 |
| 1_$t_5$ | |
| SYSTEM.BASIS | $t_0$ |
| 1_$t_7$ | |
| SYSTEM.BASIS | $t_0$ |

*Fig. 6*

| 1 [$t_5$] | |
|---|---|
| First_Name | Collin |
| Last_Name | Kelley |
| Phone | ["610-555-7777", "576-555-0123"] |
| License_Number | LP275 |
| Status | Valid |
| Timestamp | $t_5$ |

*Fig. 7*

| 2 [$t_0$] | |
|---|---|
| First_Name | Collin |
| Phone | ["610-555-7197", "484-555-9823"] |
| timestamp | $t_0$ |
| nextVersion | $t_5$ |
| 2 [$t_5$] | |
| First_Name | Collin |
| Phone | ["610-555-7777", "576-555-0123"] |
| timestamp | $t_5$ |
| nextVersion | $t_7$ |
| 2 [$t_7$] | |
| First_Name | Collin |
| Phone | ["610-555-7777", "576-555-4444"] |
| timestamp | $t_7$ |
| nextVersion | null |

*Fig. 8*

COMPUTER-IMPLEMENTED METHODS AND COMPUTER SYSTEMS FOR MASTER DATA MANAGEMENT LEVERAGING A NON-RELATIONAL DATABASES FOR DYNAMICALLY AGGREGATING DATA OF DISTINCT FORMATS AND/OR CONTENT

RELATED APPLICATIONS

This application claims the priority of U.S. provisional application Ser. No. 61/798,744, filed Mar. 15, 2013 which is incorporated herein by reference in its entirety for all purposes.

TECHNICAL FIELD

In some embodiments, the instant invention is related to computer-implemented methods and systems for master data management leveraging non-relational databases for dynamically aggregating data of distinct formats and/or content.

BACKGROUND OF INVENTION

In some embodiments, this invention intersects the field of Master Data Management (MDM) and data warehousing. MDM focuses on data stewardship across disparate data sources, also known as feeds. Typically, the objective of MDM is to provide a single master file that consolidates information from those disparate feeds, eliminates inconsistencies, and ensures data quality. Typically, data warehousing is a technical approach one could use to implement MDM. Typically, data warehousing is a data aggregation and modeling technique whereby data is centralized, standardized and maintained in a single system. Typically, data warehousing includes dimensional analysis of data, including a temporal dimension. Traditionally, relational databases have been the storage mechanism of choice for large data warehouses. Typically, non-relational databases use a Distributed Hash Table (DHT) as their base data structure.

BRIEF SUMMARY OF INVENTION

In some embodiments, the instant invention provides for a computer-implemented method that includes at least the following steps of: electronically receiving, by at least one specialized computer system, at least ten data feeds, where each data feed contains information associated with a plurality of healthcare-related entities, where a data schema of each data feed is unknown to the at least one computer system prior to the receipt of each data feed, and where the at least one specialized computer system includes at least one specialized computer machine comprising a non-transient memory having at least one region for storing specific computer executable program code and where the at least one specialized computer machine is specifically programmed to perform at least one step of the computer-implemented method; automatically determining, by the at least one specialized computer system, in real-time, across the received data feeds, for each of the plurality of healthcare-related entities, at least the following entity information: i) at least one first type data fragment identifying at least one first identifier associated with at least one first healthcare-related entity from the plurality of healthcare-related entities; and ii) a plurality of second type data fragments, where each second type data fragment contains at least one item of information about the at least one first healthcare-related entity identified by the at least one first identifier; automatically storing, by the at least one specialized computer system, each time when the entity information for the at least one first healthcare-related entity is received, the entity information for the at least one first healthcare-related entity across a plurality of distributed non-relational computer databases, by: i) creating, for each time when the entity information for the at least one first healthcare-related entity is received, a plurality of records, where each record includes at least one first row with a plurality of columns, where the at least one first row is associated with the at least one first identifier of the at least one first healthcare-related entity from the plurality of healthcare-related entities and where each column of the at least one first row has: 1) a name composed of a hierarchical path to a content of each column, where the hierarchical path includes at least: a) a row identifier of that least one first row and b) at least one second identifier that is uniquely identifies at least one characteristic of the at the least one item of information of at least one second type data fragment, and 2) the at least one item of information of the at least one second type data fragment; or ii) updating, for each time when the entity information for the at least one first healthcare-related entity is received, the at least one first record based on: 1) determining the name of the column based on the hierarchical path, and 2) recoding the least one item of information of the at least one second type data fragment about the at least one first healthcare-related entity in a column identified by the determining the name of the column; analyzing, by the at least one specialized computer system, the plurality of distributed non-relational computer databases to determine a plurality of records associated with the at least one first healthcare-related entity; and determining, by the at least one specialized computer system, at least one first verified record of the at least one first healthcare-related entity at a particular time, where the at least one first verified record based at least in part on the entity information of the at least one first healthcare-related entity that has been stored across the plurality of distributed non-relational computer databases at each time when the entity information of the at least one first healthcare-related entity has been received.

In some embodiments, the at least one first healthcare-related entity is selected from the group of: physicians, hospitals, healthcare insurance organizations, pharmacies, healthcare industry certification authorities, and healthcare government agencies.

In some embodiments, the analyzing the plurality of distributed non-relational computer databases includes at least: creating a first plurality of relationships that tracks, over plurality of times, the entity information of the at least one first healthcare-related entity across the received data feeds; where the first plurality of relationships comprises relationships among: i) a plurality of fragment vertexes, where each fragment vertex corresponds to each second type data fragment containing the at least one item of information about the at least one first healthcare-related entity; ii) a plurality of entity vertexes, where each entity vertex corresponds to the entity information for the at least one first healthcare-related entity received at each time; and iii) a plurality of load vertexes, where each load vertex corresponds to a particular data feed with the entity information for the at least one first healthcare-related entity received at each time; and where the determining the at least one first verified record of the at least one first healthcare-related entity at the at particular time is further based on the first plurality of relationships among the plurality of fragment vertexes associated with the at least one first healthcare-related entity, the plurality of entity vertexes associated with the at least one first healthcare-related entity, and the plurality of load vertexes associated with the at least one first healthcare-related entity.

In some embodiments, the analyzing the plurality of distributed non-relational computer databases includes at least: matching the items of information about the at least one first healthcare-related entity across the plurality of fragment vertexes associated with the plurality of entity vertexes that corresponds to the at least one first healthcare-related entity, where the matching is based, at least in part, on at least one of the following: i) priority ranking among the plurality of data feeds, and ii) an age of data; and traversing the first plurality of relationships to identify at least one verified vertex that corresponds to the at least one first verified record of the at least one first healthcare-related entity at the particular time.

In some embodiments, the creating the plurality of relationships further includes at least: identifying, for each entity vertex, at least one data source, from which the entity information has been received, in the received data feeds.

In some embodiments, the analyzing the plurality of distributed non-relational computer databases further includes at least: determining a subset of the plurality of entity vertexes that are related based at least in part on matching the items of information about the at least one first healthcare-related entity across the plurality of verified vertexes; creating a second plurality of relationships to identify entities for consolidation based on the subset of the plurality of entity vertexes; and consolidating the identified entities into at least one second verified record.

In some embodiments, the analyzing the plurality of distributed non-relational computer databases further includes at least: creating at least one first organization vertex identifying at least one first organization that is related to a plurality of entities based, at least in part, on at least one first matched item of information among the plurality of fragment vertexes associated with the plurality of entity vertexes.

In some embodiments, the analyzing the plurality of distributed non-relational computer databases further includes at least: analyzing the plurality of relationships among the plurality of fragment vertexes, the plurality of entity vertexes, and plurality of load vertexes to determine that the at least one first organization is invalid; and creating at least one second organization vertex identifying at least one second organization that is related to the plurality of entities based, at least in part, on at least one second matched item of information among the plurality of fragment vertexes associated with the plurality of entity vertexes.

In some embodiments, the plurality of second type data fragments includes at least one hundred second type data fragments associated with the at least one first healthcare-related entity.

In some embodiments, the received data feeds include at least one million records related to the plurality of healthcare-related entities.

In some embodiments, the instant invention provides for a computer-implemented system that includes at least the following components/modules: at least one specialize computer machine that includes at least: a non-transient memory having at least one region for storing particular computer executable program code; and at least one processor for executing the particular program code stored in the memory, where the particular program code is configured to at least perform the following operations: electronically receiving, at least ten data feeds, where each data feed contains information associated with a plurality of healthcare-related entities, where a data schema of each data feed is unknown to the at least one computer system prior to the receipt of each data feed; automatically determining, in real-time, across the received data feeds, for each of the plurality of healthcare-related entities, at least the following entity information: i) at least one first type data fragment identifying at least one first identifier associated with at least one first healthcare-related entity from the plurality of healthcare-related entities; and ii) a plurality of second type data fragments, where each second type data fragment contains at least one item of information about the at least one first healthcare-related entity identified by the at least one first identifier; automatically storing, each time when the entity information for the at least one first healthcare-related entity is received, the entity information for the at least one first healthcare-related entity across a plurality of distributed non-relational computer databases, by: i) creating, for each time when the entity information for the at least one first healthcare-related entity is received, a plurality of records, where each record comprises at least one first row with a plurality of columns, where the at least one first row is associated with the at least one first identifier of the at least one first healthcare-related entity from the plurality of healthcare-related entities and where each column of the at least one first row has: 1) a name composed of a hierarchical path to a content of each column, where the hierarchical path comprises: a) a row identifier of that least one first row and b) at least one second identifier that is uniquely identifies at least one characteristic of the at the least one item of information of at least one second type data fragment, and 2) the at least one item of information of the at least one second type data fragment; or ii) updating, for each time when the entity information for the at least one first healthcare-related entity is received, the at least one first record based on: 1) determining the name of the column based on the hierarchical path, and 2) recoding the least one item of information of the at least one second type data fragment about the at least one first healthcare-related entity in a column identified by the determining the name of the column; analyzing, the plurality of distributed non-relational computer databases to determine a plurality of records associated with the at least one first healthcare-related entity; and determining, at least one first verified record of the at least one first healthcare-related entity at a particular time, where the at least one first verified record based at least in part on the entity information of the at least one first healthcare-related entity that has been stored across the plurality of distributed non-relational computer databases at each time when the entity information of the at least one first healthcare-related entity has been received.

BRIEF DESCRIPTION OF THE FIGURES

The present invention will be further explained with reference to the attached drawings, wherein like structures are referred to by like numerals throughout the several views. The drawings shown are not necessarily to scale, with emphasis instead generally being placed upon illustrating the principles of the present invention. Further, some features may be exaggerated to show details of particular components.

FIG. 1 illustrates an illustrative example in accordance with some embodiments of the present invention.

FIG. 2 illustrates another illustrative example in accordance with some embodiments of the present invention.

FIG. 3 illustrates yet another illustrative example in accordance with some embodiments of the present invention.

FIG. 4 illustrates yet another illustrative example in accordance with some embodiments of the present invention.

FIG. 5 illustrates yet another illustrative example in accordance with some embodiments of the present invention.

FIG. 6 illustrates yet another illustrative example in accordance with some embodiments of the present invention.

FIG. 7 illustrates yet another illustrative example in accordance with some embodiments of the present invention.

FIG. 8 illustrates yet another illustrative example in accordance with some embodiments of the present invention.

Figure 9:
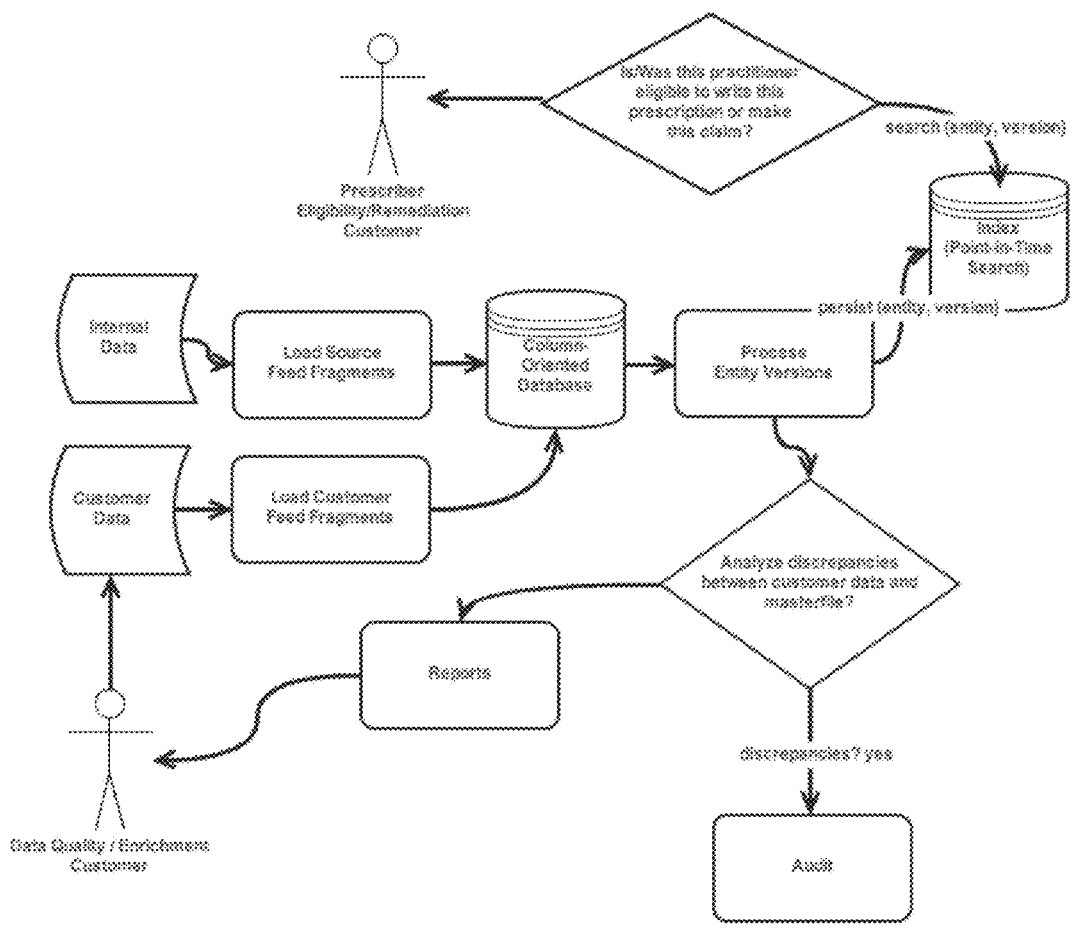
FIG. 9 illustrates yet another illustrative example in accordance with some embodiments of the present invention.

In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

DETAILED DESCRIPTION OF INVENTION

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive. Any alterations and further modifications of the inventive feature illustrated herein, and any additional applications of the principles of the invention as illustrated herein, which would normally occur to one skilled in the relevant art and having possession of this disclosure, are to be considered within the scope of the invention.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

In some embodiments, the invention leverages a non-relational storage mechanism for the purposes of Master Data Management. In some embodiments, the invention stores data in a schema-optional, column-oriented database. In some embodiments, the invention does not require any pre-definition and each row in a table can have a differing number of columns. In some embodiments, the invention leverages the inherent flexibility in a column-oriented database to accommodate disparate and changing feed schemas.

In some embodiments, the invention also leverages an indexing engine/search server to provide transactional query capabilities across the history of the master file, and across all feeds. In some embodiments, the invention provides a translation mechanism from structured/relational feeds to column-oriented storage including a temporal dimension. In some embodiments, that storage is then kept in synch with the indexing engine, which leverages a different data structure to support transactional queries across time.

In some embodiments, the instant invention utilizes a native flexible mechanism for distributed scalable storage addresses both volume and velocity, and accommodating the disparate formats of the incoming data feeds (i.e., variety).

It is understood that at least one aspect/functionality of various embodiments described herein can be performed in real-time and dynamically. As used herein for some embodiments of the instant invention, the term "real-time" means that, for example, database updates (e.g., record updates, record creation) occurs without noticeable delay from a time that data is received by computer machines of the computer systems of the instant inventions and/or there is no noticeable delay in time passed between subsequent interactions within the computer systems of the instant inventions. For example, in some embodiments, the delay is no more than 1 minute. In some embodiments, the delay is no more than 1 second. For example, in some embodiments, the delay is no more than 1 minute. In some embodiments, the delay is no more than 10 seconds. In some embodiments, the delay is between less than 1 second and 1 minute.

As used herein, the term "dynamic(ly)"/"automatically" means that an event/action that can occur without any human intervention. The event/action may be in real-time, hourly, daily, weekly, and/or monthly.

In some embodiments, the invention focuses on Master Data Management over time, whereby a user can get a consolidated view of a record, or set of records at any point-in-time. In some embodiments, the invention allows for integration into transactional systems and is capable of servicing transactional requests for given any point-in-time. In some embodiments, the inventive systems of the instant invention permit ongoing management of multiple streams of data with dynamic structure to aggregate/consolidate those disparate and/or distinct data stream into at least one masterfile/database.

In some embodiments, the inventive systems of the instant invention receive data from numerous sources (feeds), versioning input from those feeds over time, accommodating structural changes. In some embodiments, the inventive systems of the instant invention then matches fragments of data across feeds, and produces a unified version of the consolidated entity resolving all discrepancies and conflicts between the data feeds. In some embodiments, the inventive systems of the instant invention receive entity fragments, process and store the received data with hierarchical structure utilizing a non-relational distributed storage mechanism. In some embodiments, the consolidated data structure(s) and/or values of the data stored in the consolidated data structure(s) change over time. In some embodiments, the inventive systems of the instant invention avoid the use of locking mechanisms during processing of the received data. In some embodiments, the inventive systems of the instant invention utilize an indexing mechanism that allows searching stored/received data as of any historical point-in-time.

In some embodiments, data streams received by the computer machine(s) of the computer system(s) of the instant invention can include at least 10 data points of information about a particular entity. In some embodiments, data streams received by the computer machine(s) of the computer system(s) of the instant invention can include at least 50 data points of information about a particular entity. In some embodiments, data streams received by the computer machine(s) of the computer system(s) of the instant invention can include at least 100 data points of information about a particular entity. In some embodiments, data streams received by the computer machine(s) of the computer system(s) of the instant invention can include at least 500 data points of information about a particular entity. In some embodiments, data streams received by the computer machine(s) of the computer system(s) of the instant invention can include at least 1000 data points of information about a particular entity. In some embodiments, data streams received by the computer machine(s) of the computer system(s) of the instant invention can include between 5 and 1000 data points of information about a particular entity. In some embodiments, data streams received by the computer machine(s) of the computer system(s) of the instant invention can include between 10 and 1000 data points of information about a particular entity.

In some embodiments, data streams received by the computer machine(s) of the computer system(s) of the instant invention can include between 10 and 1000 records related to various entities. In some embodiments, data streams received by the computer machine(s) of the computer system(s) of the instant invention can include between 10 and 10,000 records related to various entities. In some embodiments, data streams received by the computer machine(s) of the computer system(s) of the instant invention can include between 10 and 100,000 records related to various entities. In some embodiments, data streams received by the computer machine(s) of the computer system(s) of the instant invention can include between 100,000 and 1 million of records related to various entities. In some embodiments, data streams received by the computer machine(s) of the computer system(s) of the instant invention can include between 10 and 1 million of records related to various entities. In some embodiments, data streams received by the computer machine(s) of the computer system(s) of the instant invention can include between 10 and 10 million of records related to various entities. In some embodiments, data streams received by the computer machine(s) of the computer system(s) of the instant invention can include between 10 and 100 million of records related to various entities. In some embodiments, data streams received by the computer machine(s) of the computer system(s) of the instant invention can include at least 10,000 records related to various entities. In some embodiments, data streams received by the computer machine(s) of the computer system(s) of the instant invention can include at least 100,000 records related to various entities. In some embodiments, data streams received by the computer machine(s) of the computer system(s) of the instant invention can include at least 1 million of records related to various entities. In some embodiments, data streams received by the computer machine(s) of the computer system(s) of the instant invention can include at least 10 million of records related to various entities.

In some embodiments, the instant invention addresses data warehousing needs associated with Master Data Management (MDM) by providing scalability. In some embodiments, the instant invention addresses a problem of sharding—distribution of a database across a larger number of machines in the absence of a natural partitioning strategy (i.e. sharding). In some embodiments, the instant invention addresses allows to process certain amount of data (i.e. volume) in the system faster than conventional relational databases can (i.e. velocity). In some embodiments, the instant invention utilizes a non-relational database with a Distributed Hash Table (DHT) as its base data structure, which provides a native sharding mechanism allowing databases to linearly scale with the volume of the data.

In some embodiments, the instant invention processes inputs of data whose structure is unknown in advance. The feeds come from disparate sources; sometimes those are structured sources from a relational system, sometimes not (e.g. harvesting data from the internet). In some embodiments, specifically programmed computer machines of the inventive computer systems of the instant invention accommodate varying amounts of structure in the incoming feed, then impose enough structure to reason and/or analyze the data.

In some embodiments, specifically programmed computer machines of the inventive computer systems of the instant invention accommodate changing schemas seamlessly on a scheduled and/or ad hoc basis. In some embodiments, the instant invention allows a single view of information (e.g., a single view of a doctor over time) drawn from databases having incompatible schema changes. For example, what if a feed originally associated a phone number directly with a doctor, but introduced a change to the structure such that phone numbers were associated with addresses, which are then associated with doctors.

In some embodiments, the inventive systems of the instant invention provide unified consolidated view(s) of entities as they change over time, even in the event of incompatible schema changes. In some embodiments, the instant invention enables the user to search across all entities as of a point-in-time. In some embodiments, the inventive systems of the instant invention include an index for point-in-time queries for data.

In some embodiments, as used herein, a feed means an incoming source of data. In some embodiments, the feed may have multiple streams of data, each of which may contain multiple attributes. FIG. 1 depicts an example of incoming feed data, whereby fragments of entities (e.g., information about particular medical practitioners) are distributed across three different and disparate data streams. In some embodiments, the exemplary sources are tab-delimited computer files/databases containing practitioners, phones, and state licenses information named PRACT.tab, PHONE.tab, and STATE_LICENSE.tab respectively. For example, FIG. 1 depicts a sample feed from a government organization that supplies practitioner names, phone numbers, and state license information.

In some embodiments, feeds may supply information in real-time transactions or in bulk. In some embodiments, the computer machine(s) of the computer system(s) of the instant invention receive(s) data feeds in bulk as tab-delimited files. For example, in some embodiments, a particular feed can have three streams: practitioners (supplied in the PRACT.tab file), phone numbers (supplied in the PHONE.tab file), and state license information (supplied in the STATE_LICENSE.tab file).

In some embodiments, the disclosed invention processes feeds of data by incorporating the fragments from streams into a non-relational storage mechanism. In some embodiments, as referred herein for purposes of this disclosure, a non-relational storage mechanism means a storage mechanism that does not have in-built methodology of relating objects. Typically, the non-relational storage systems sacrifice relationships and constraints for speed and scalability.

In some embodiments, the computer machine(s) of the computer system(s) of the instant invention leverage(s) column-oriented database(s) as its/theirs non-relational storage mechanism. For example, each entity in its entirety can persist in a single row in the database(s), using an arbitrary number of columns. Specifically, in some embodiments, each fragment within a stream becomes a column in the non-relational storage mechanism.

In some embodiments, the computer machine(s) of the computer system(s) of the instant invention determine(s) the column name using at least one layout file. The following is a sample layout file for the data in FIG. 1.

ENTITY_KEY=ID
PRACT [ID]{
   PHONE [ID, PHONE_ID]
   STATE_LICENSE [ID, STATE_LICENSE_ID]
}

In some embodiments, an exemplary layout file specifies the relationships between fragments in streams, allowing the system to properly construct keys that uniquely identify each fragment and relate it to the whole entity. In some embodiments, the keys become column names. In some embodiments, for each fragment in each stream, the method for fragment processing proceeds as follows:

processFragment(fragment) {
   rowKey=concatenate(entityKey(layout), timestamp)
   columnKey=determineColumnKey(fragment, layout)
   write(rowkey, columnKey, fragment)
}

In some embodiments, the entityKey is provided by the layout, and defines the column or columns that uniquely identify fragments belonging to the same entity. In some embodiments, entityKey is the ID column.

In some embodiments, the columnKey has two components, a path and a composite unique identifier. In some embodiments, the path is the hierarchical position of the fragment in the entities logical structure. In some embodiments, the hierarchical structure is defined in the layout. The example layout defines PHONE and STATE_LICENSE as child fragments of PRACT. In some embodiments, the hierarchical structure can be arbitrarily deep. In addition to the path, in some embodiments, the columnKey also contains the composite unique identifier that allows a single row to contain multiple fragments of the same type, from the same stream, without a collision on the column name.

In this illustrative example, the computer machine(s) of the computer system(s) of the instant invention the invention utilize(s) the rowKey syntactically as ID [timestamp] and utilizes the column key syntactically as PATH [composite_key]. FIG. 3 depicts the results of the transformation. In the sample data, assuming the data was loaded at time $t_0$. The fragment identified by LICENSE_ID 502 transforms into the following keys:

rowKey=1 [$t_0$]
   columnKey=PRACT.STATE_LICENSE [1.502]

The value for each of the columns is then the entire fragment as key-value pairs.

In some embodiments, each row/line in the stream became a column in the storage mechanism. That column is stored under a row identified by a subset of columns in the fragment. The column name is a composite of the hierarchical path to the data, combined with a second subset of columns that uniquely identifies that piece of data in the system.

In some embodiments, the invention allows its inventive databases to be scalable horizontally across distributed resources (e.g., a plurality of computer machines with electronic databases/files). In some embodiments, each fragment can be processed independently, which means processing can be distributed across a set machines to achieve linear scalability.

In some embodiments, the fragment processing method is idempotent. As referred herein for purposes of this disclosure, idempotent operations are operations that can be performed safely over and over again because the state of the system is not affected on subsequent invocations of an idempotent operation. Due to distributed implementation, when connectivity is lost to a node to which an operation was already distributed and the operation must be retried on a different node, the instant invention tolerates both nodes performing the same operation.

In some embodiments, the use of the idempotent operations by the instant invention results in lessening the demands on the infrastructure and/or allows the process to scale linearly because the system can tolerate processing the same record more than once. Specifically, in some embodiments, if a set of fragments is distributed to a machine for processing, and the inventive systems of the instant invention lose connectivity with that particular machine, the fragments can safely be distributed to another machine. In some embodiments, the instant invention guarantees the integrity of data in the system state by processing each record at least once.

In some embodiments, the instant invention accommodates changes in the values and structure of the data as detailed further. In some embodiments, the invention can process complete streams of data as well as partial transactions. As referenced herein, in some embodiments, a complete data stream (or stream) means a data stream that contains all fragments for an entity at a specific time. As referenced herein, in some embodiments, a partial data stream (or a partial stream) means a data stream that only contains mutated fragments, fragments that have changed since the last time that entity was processed. In some embodiments, the inventive methods/principles described below with respect to the partial streams are equally applicable to complete stream processing.

In some embodiments, fragments in partial streams must include an operation code that specifies the desired mutation. In some embodiments, the operation code is one of: UPDATE or DELETE. In some embodiments, each fragment is then merged into the previous version of the entity from the most current timestamp available. In some embodiments, to accommodate partial updates the fragment processing method is enhanced as follows:

processFragment(fragment, timestamp){
   rowKey=concatenate(entityKey(layout), timestamp)
   columnKey=determineColumnKey(fragment, layout)
   oldRow=fetchMostRecent(rowKey)
   newRow=merge(rowKey, fragment)
   write(rowkey, newRow)
}

The fetchMostRecent method simply retrieves the row with timestamp $t_{old}$, maximizing $t_{old}$ where $t_{old}$<timestamp. In some embodiments, this query is supported by an index. In some embodiments, rowKeys are composite keys backed by a wide-row index.

In some embodiments, the instant invention utilizes the merge method to examine the operation code on the fragment and adjust the row accordingly. In some embodiments, each row is effectively a key-value store. In some embodiments, for an UPDATE, the column is set on the row overwriting the previous version, or adding the row if it did not previously exist on the row. In some embodiments, for a DELETE, the column is removed from the row. In some embodiments, after the merge, the entire entity is written back to the repository as a new row at the new timestamp.

The illustrative results of processing the partial stream at times $t_5$ and $t_7$ is depicted in FIG. 5 which represents the state of the non-relational storage after the updates depicted in FIG. 3.

In some embodiments, the instant invention allows to merge the fragment into the old version. Specifically, in some embodiments, the instant invention allows to process two fragments that are from different points in time, for the same entity. Fig. depicts the example data of FIG. 1 when stored in the non-relational repository. For instant, FIG. 3 shows the transformation from row-orientation to column-orientation, demonstrating that row-orientation can accommodate relationships of arbitrary cardinality. For example, in some embodiments, the instant invention allows the partial updates of FIG. 3 that are processed concurrently the merge for t5 and the merge for t7 that might both use t0 as a basis. In some embodiments, the instant invention detects such situations and resolves them without sacrificing scalability. In some embodiments, the instant invention maintains a processing ledger as depicted in FIG. 6. FIG. 6 depicts the added processing ledger that allows an exemplary computer system in accordance with some embodiments of the instant invention to process each transaction independently, without sacrificing the ability to detect issues in data integrity.

In some embodiments, in the ledger, the inventive systems of the instant invention maintain what version each row was based on. In some embodiments, the inventive systems of the instant invention then periodically and/or automatically check this ledger for temporal violations, where strict ordering of the timestamps is not maintained. In some embodiments, the periodical check are based, at least in part, on at least one of condition:
   a predetermined set time, and
   a predetermined trigger condition.

In some embodiments, for any timestamp, for each rowkey, the inventive computer systems of the instant invention perform the following:
verify(id, timestamp){
    lastVersion=−1
    for each ordered timestamp $t_m$<timestamp for id {
    if BASIS time !=lastVersion
        replay($t_n$)
    lastVersion=t.
    }
}

In some embodiments, the above procedure verifies that the rows associated with id are consistent up to timestamp. In some embodiments, utilizing the above procedure, the inventive systems of the invention can then trust any data prior to that timestamp. In some embodiments, the periodicity of the verification can be tuned to align with availability requirements. Once verified, the inventive systems would prevent writes to times prior to timestamp, or it would need to re-run verification. In some embodiments, there is a sliding temporal window for writes.

In some embodiments, the inventive systems of the invention also accommodate changes to structure. In some embodiments, FIG. 4 introduces a new stream that was not present in the initial feed. For example, FIG. 3 depicts data from a feed that constitutes two separate partial updates for phones. The first table represents a partial update received as a tab-delimited file at $t_5$ and the second table represents a separate update received at $t_7$. Specifically, in FIG. 4, it adds addresses to practitioners. In some embodiments, to accommodate the structural change, the inventive systems utilize a new version of the layout. The new layout can include the address stream:
ENTITY_KEY=ID
PRACT [ID] {
   PHONE [ID, PHONE_ID]
   STATE_LICENSE [ID, STATE_LICENSE_ID]
   ADDRESS [ID, ADDR_ID]
}

With the new layout, in some embodiments, the inventive systems load data using the same method previously described. In some embodiments, to accommodate fetching records from any point in time, it is a matter of applying the right layout. In some embodiments, the inventive systems of the invention do this by keeping metadata regarding the dates of applicability for a layout.

In some embodiments, the inventive systems of the invention also provide a scalable mechanism for temporal search, allowing any user or system to search the data, limiting that search to only versions of records pertinent to that time period. In some embodiments, the instant invention leverages a document-indexing engine that supports structured and unstructured searching performed by the specifically programmed computer machine(s) of the computer system(s) of the instant invention.

In some embodiments, indexing engines of the instant invention index a set of fields. In some embodiments, those fields are either single or multi-value. In some embodiments, the final step in processing a record is indexing. In this step, in some embodiments, the hierarchical structure maintained in the non-relational storage mechanism is converted into a flat document. For example, FIG. 7 shows a flattened record, which is, in-turn, added to the index.

In some embodiments, the inventive systems of the instant invention allow to translate values in a way that establishes relationships between related fields. For example, since a practitioner can have multiple addresses, the index would allow for multiple values under the field "City" and "State". With a practitioner, John Doe, that lives in Springfield, Pa. and Joplin, Mo., this would result in the following multivalued document:
City: ["Springfield", "Joplin"]
State: ["PA", "MO"]

If we query for practitioners in Springfield, Mo. using a query where City="Springfield" and State="MO" will result in a false positive returning John Doe since the index did not relate City and State. To resolve this issue, in some embodiments, the instant invention adds semantic relationships to the layout as follows:
ENTITY_KEY=ID
PRACT [ID] {
   PHONE [ID, PHONE_ID]
   STATE_LICENSE [ID, STATE_LICENSE_ID]
   ADDRESS [ID, ADDR_ID] {
   System.JOIN_ON_INDEX[City, State]
   }
}

In some embodiments, the System.JOIN directive instructs the system to join those fields when indexing, yielding a single multi-valued. The same sample practitioner would result in the following document:
City_State: ["Springfield_PA", "Jopin_MO"]

In some embodiments, the inventive systems of the instant invention provide the point-in-time searching. In order to query a point-in-time, in some embodiments, the inventive index includes all versions of all entities, but the range of a search is limited to only the single version of that entity pertinent to the time period. To support these types of queries, the inventive systems of the invention include the timestamp in the indexed document as shown in FIG. 7.

In some embodiments, the inventive systems of the instant invention only consider the version of the document containing the maximum timestamp less than the point-in-time of interest. In some embodiments, the inventive systems of the instant invention employ the processing ledger that contains the time series information for a particular entity. In some embodiments, the inventive systems of the instant invention then add this information to the documents in the index. In some embodiments, the inventive systems of the instant invention enhance the verification method to also update the documents as follows:

verify(id, timestamp){
   lastVersion=-1
   for each ordered timestamp $t_m$<timestamp for id {
     ...
     update_index(id_lastVersion, "nextVersion=$t_n$")
   }
}

For example, the update_index function modifies the document associated with the previous version of record and adds a field nextVersion that contains the current records timestamp. The result is shown in FIG. 8. For example, this process effectively forms a linked list of versions in the index, each document containing a pointer to the next version of that document.

In some embodiments, the inventive systems of the instant invention then use this added structure/information in our query, which simplifies the query. The previous query becomes:

select documents where gender=male
   and City_State=Springfield_MO
   and timestamp <$t_5$
   and (nextVersion=null OR nextVersion >$t_5$)

This final clause in the query limits the documents considered to only those that straddle the point-in-time under consideration, with a timestamp before and either no next version, or a next version that is after the point-in-time under consideration.

As detailed above for some embodiments, the inventive systems of the instant maintain versions of entities over time, with changing structure, while enabling distributed processing and real-time/transactional search.

In some embodiments, the inventive systems of the instant invention leverage batch-processing mechanisms to perform the operations described above. Specifically, some embodiments may leverage "Hadoop". The term "Hadoop" refers to an open source map/reduce framework. When the inventive systems of the instant invention use Hadoop, the above operations are performed as map/reduce operations. Fragments are processed during the map phase of education. In some embodiments, fragments are then grouped by the entity that they comprise, and the reduce phase performs all entity level operations (e.g., versioning).

In embodiments that require real-time processing, the inventive systems of the instant invention leverage a distributed processing framework known as "Storm". In some embodiments, utilizing "Storm" allows users to articulate data flows in topologies. In some embodiments, topologies of Storm comprise spouts and bolts. Spouts emit tuples. Tuples contain data, which are processed by bolts. In some embodiments, the processing is separated into two topologies: fragment and entity processing. In the fragment topology, a spout emits tuples containing fragments, which are then distributed to all nodes in the Storm cluster and processed independently. When all fragments are processed for an entity, the spout in the entity processing topology reads the entire entity and processes the versioning, etc. Storm guarantees the each tuple is processes at least once, but tuples may be replayed multiple times. Thus, in some embodiments, the inventive systems of the instant invention use the Storm framework because all the operations of the inventive systems of the instant invention are idempotent.

While the above description provide specific examples of usage of certain frameworks, those examples are not intended to be restrictive but illustrative, and thus the above disclosed frameworks can work with other types of non-relational storage mechanisms, and that the usage of the above described frameworks are equally applicable to other storage mechanisms that are not column-oriented. For example, some embodiments of the instant invention leverage a document-oriented database, where the entity id may be used as the document id, and the document may contain the fragment data, one key per fragment.

In some embodiments, the inventive systems use an equivalent data model. For example, the temporal dimension of the entity may be pushed down into the columnar data.

In some embodiments, the inventive systems of the instant invention can be applied to analyze and/or track at least the following: prescriber remediation, data quality and enrichment, prescriber eligibility, and/or spend analysis.

For example, prescriber eligibility addresses the need to determine if a practitioner was eligible to issue a particular prescription based on their licenses, sanction information, and specialty. In some case, for prescriber eligibility, it can be critical to have the most current information on which to base the decisions. Additionally, for compliance and auditing, in some embodiments, the inventive computer systems of the instant invention maintain the data over time, to be able to report out historically why a decision was made.

In some embodiments, the instant invention is applicable to prescriber remediation since Government and Payer want the ability to detect fraud, waste and abuse. In some embodiments, the instant invention allows interested parties to identify retroactively potentially fraudulent claims and prescriptions by maintaining entities over time and allowing real-time search of that data as of a particular point in time.

In some embodiments, the instant invention allows users to align their data with the masterfile/database produced in accordance with at least some principles of the instant invention. For example, for compliance reasons pharmaceutical companies need their expenses aligned against a current practitioner universe to report out on, and audit expenditures. Enriching the expenses with current practitioner information is one key component in meeting that demand. As part of this process, discrepancies between the data streams can be audited and reconciled in accordance with principles of the instant invention described above.

In some embodiments, the instant invention allows linking entities across feeds via match processing, consolidating those entities, identifying logical groupings of entities, and assigning affiliations between entities and those groups (i.e. organizations).

In some embodiments, the invention uses at least one graphical presentation ("graph") to support the inter-feed processes. In some embodiments, in the graph, entity fragments are represented as vertices. In such graph, there are two edge types that convey "comprises" and "transformed" relationships.

Figure 10:
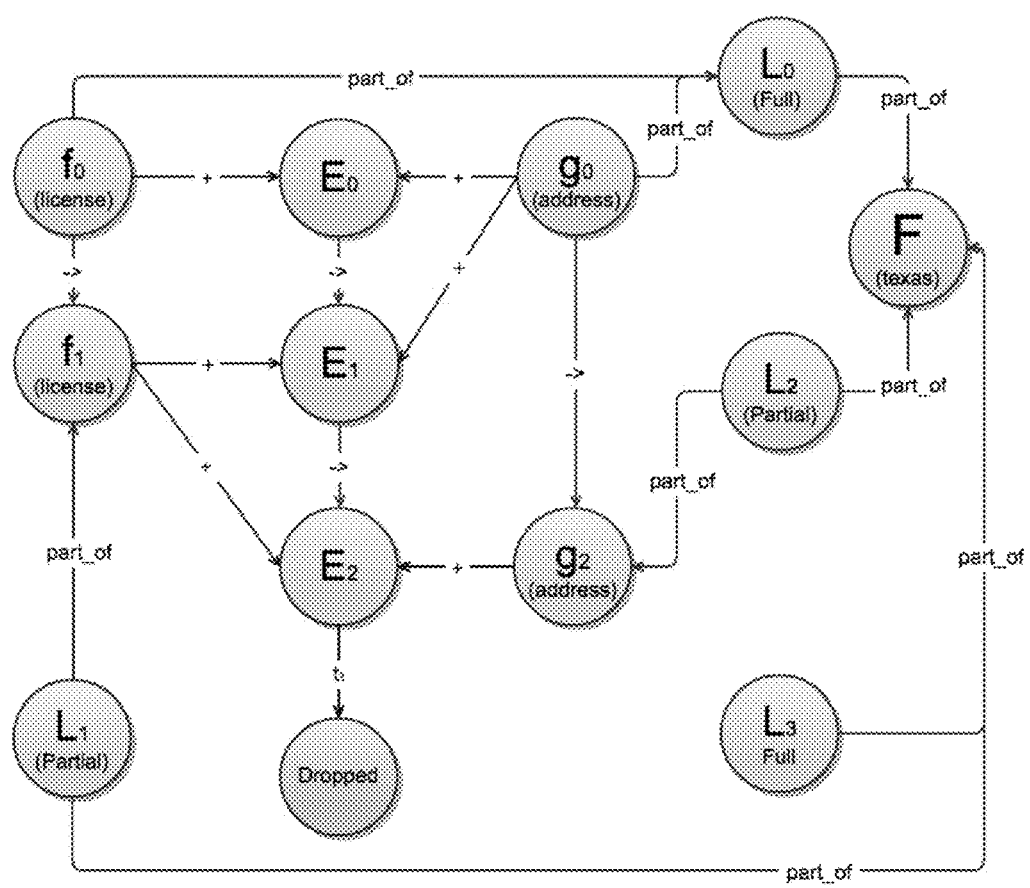
FIG. 10 illustrates yet another illustrative example in accordance with some embodiments of the present invention.

Referring to FIG. 10 that illustrates an exemplary graph in accordance with some principles of the instance invention. In FIG. 10, for example, comprising edges are annotated with a "+" and transformation edges are annotated with a "→" symbol. In FIG. 10, there are two vertex types: fragment and entity. The vertices f and g are fragment types, and the E vertices are entity types. In some embodiments, for fragment types, the subscript on each vertex represents the time at which the system received that data. In some embodiments, for entity types, the subscript on each vertex represents the time at which the system instantiated that entity vertex. Each fragment vertex has a type associated with it. For example, FIG. 10 depicts two different fragments, one address and one license comprising a single Entity evolving over time.

In some embodiments, the systems of the instant invention can utilize Load vertices (L). For example, the L vertices are load vertices in FIG. 10. In some embodiments, each load vertex represents an incoming set of data from a feed at a particular point in time. The subscript depicts the point in time at which the system received the data. In some embodiments, fragment vertices are then attached to a load via an edge that denotes "part_of", indicating that the fragment was included in that load. In some embodiments, each Load vertex is attached to a Feed vertex via an edge. In FIG. 10, F is a feed vertex, which represents a stream of data. The edges again denote that the load is "part_of" the feed.

As depicted in FIG. 10, in some embodiments, loads are either full or partial loads. In some embodiments, partial loads may only contain a subset of the entities in a feed. In some embodiments, since a patial load only contains a subset of entities, the computer system(s) of the instant invention cannot make existential decisions. That is to say that the system cannot assume that an entity ceases to exist based on its inclusion in the load. In some embodiments, partial loads may also only contain a subset of fragment types. In FIG. 10, for example, $L_0$ is a full load that contains both addresses and license information. $L_1$ is a partial load that only includes license information and $L_2$ is a partial load that only includes address information. $L_3$ is a full load that did not include the entity E. Thus, the invention constructs a new version of the entity E for that timestamp and connects it to the special vertex Dropped with an edge that indicates the time at which the system considers the record dropped from the system.

In some embodiments, the instant invention allows data stuards to interrogate the graph with queries to determine how frequently a feed delivers data, what types of data were received from a feed, the longevity of that data over time, and the potential for stale entities (when full loads are not received), etc.

FIG. 10, for example, depicts only the evolution of an entity over time, as loads are received from a single feed. In MDM, fore example, there can be often thousands of feeds of data. Thus, in some embodiments, the instant invention supplements this graph to combine data across feeds.

Figure 11:
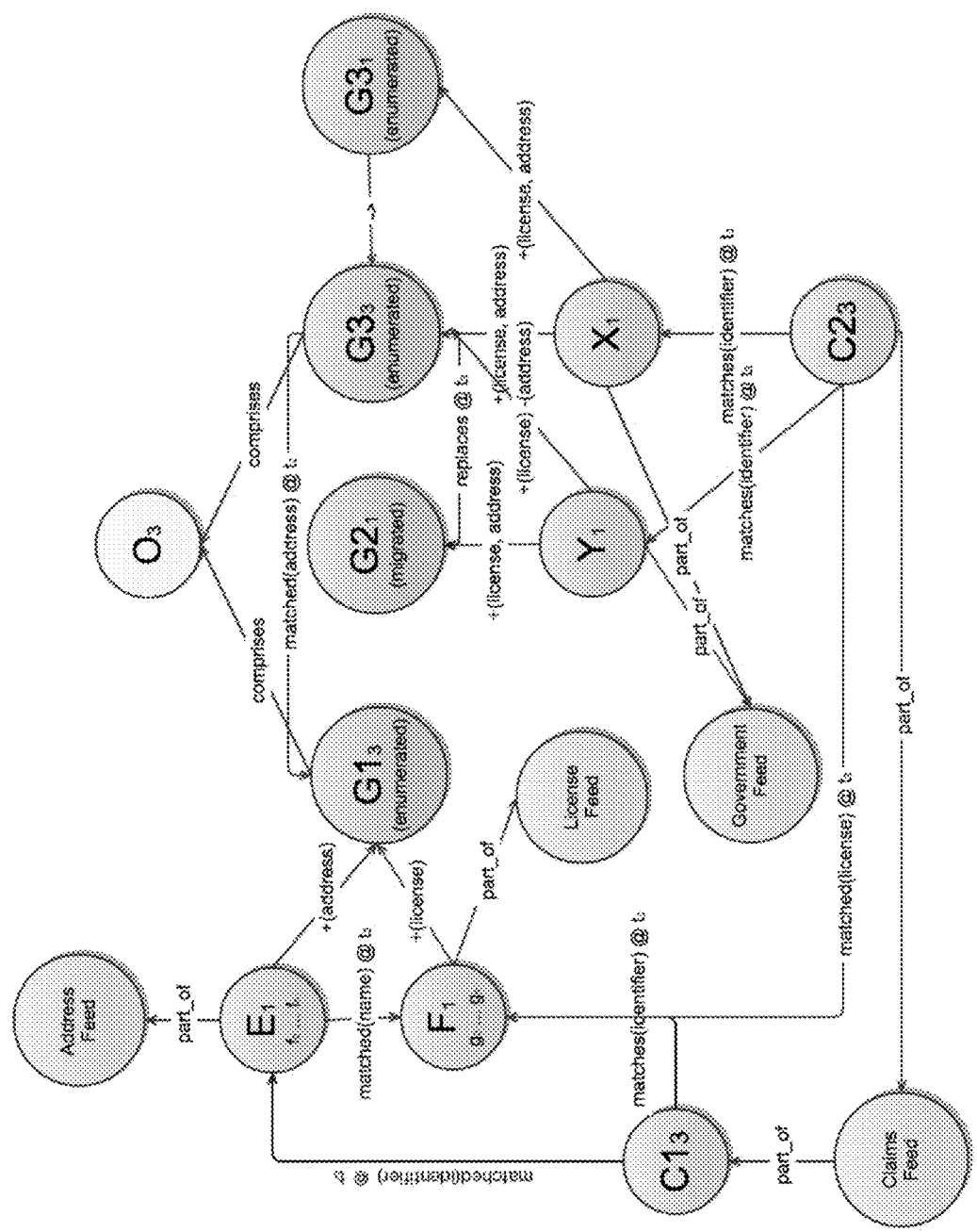
FIG. 11 illustrates yet another illustrative example in accordance with some embodiments of the present invention.

FIG. 11 depicts an exemplary illustration of an additional structure that combines data across feeds. In some embodiments, as fragments evolve over time, the inventive computer systems of the instant invention attempt to match versions of the entity across feeds using the point-in-time index described above. In some embodiments, as new fragments come into the system as part of a load, new entity versions are generated. In some embodiments, as the inventive systems of the invention generate new entity versions, they attempt to match those new versions using fuzzy logic across all fragment types comprising the entity. For example, in some embodiments, the inventive systems of the invention perform geospatial matching for the address fragments and fuzzy matching of name fragments such that the system takes into account nicknames (e.g. Bob for Robert).

In some embodiments, the graph structure captures related entities. Such capture is depicted in FIG. 11. For readability, FIG. 11, for example, omits fragment and load type vertexes. In FIG. 11, the following vertices are entities: E, F, C1, X, Y and C2. For this example, E1 is an entity from a feed that provides address information. F2 is an entity from a feed that provides license information. X and Y are entities from a government feed that provides both license and address information. C1 and C2 come from a feed of claims information.

In some embodiments, the graph of FIG. 11 is utilized for matching, consolidation and golden record enumeration. In some embodiments, a golden record is a consolidated view of an entity, where data is merged from multiple fragments, across feeds, based on feed priority, age of the data, and various other factors. In FIG. 11 example, E and F are loaded at $t_1$. They match each other based on name. In some embodiments, the inventive systems of the instant invention persist this match in an edge between the entity vertices. The edge captures which fragment type matched, and when the match occurred. In some embodiments, the inventive systems of the instant invention then uses this subgraph to determine if a new golden record should be created from the two entities.

In some embodiments, at $t_1$, given the entities have only matched on name, the inventive logic of the instant invention might not enumerate the entity because the correlation between the entities is only on a single-dimension (name). At time $t_3$, claims data is loaded. When, in some embodiments, the inventive systems of the instant invention attempt to match $C1_3$, it is able to match to both E and F based on identifiers on the claim data. This adds another dimension to the correlation. In some embodiments, based on the match, the inventive systems might then conclude that these three entities are related. Enumeration logic would examine the grouped entities and decide to create a new golden record, G1. In some embodiments, consolidation logic then chooses which fragments from which entities should be included in the consolidated golden record and create that vertex. In some embodiments, the inventive systems then create an edge between the entities and the golden record. The edges are annotated with the fragments contributed by that entity to the golden record.

In another example, the next use case depicted in FIG. 11 is that of golden record migration. In this example, Y and X are loaded at $t_1$. Since both entities have all the information the system needs for enumeration, the logic of the inventive systems decide to enumerate a golden record for each, generating G2 and G3 respectively. At $t_3$ when the inventive system loads the claims data, C2 enters the system and matches, creating a path between G2 and G3 identifying them as a single entity. In this case, the inventive system has improperly enumerated two golden records. They need to be collapsed into a single entity—i.e., a migration. The consolidation logic for that entity would re-run producing a new version of the consolidated record, G3 at $t_3$, taking both entities into account. In this example, the address information is taken from X and the license information is taken from Y. (as depicted by the edges between X, Y, and G3)

In some embodiments, the inventive system captures the migration in the graph structure by creating an edge between the golden record being replaced and the replacement vertex. In some embodiments, the system then annotates the original vertex with a "migrated" status, and the edge with a timestamp for the migration.

In some embodiments, the instant invention addresses the concept of organizations and affiliations. To capture this in the graph, the instant invention introduces a new vertex type for Organizations. In FIG. 11, O is an organization node. An example of an organization is a Group Practice that comprises many healthcare providers. In some embodiments, the instant invention includes logic that analyzes the graph and determines if the relationships are sufficient to enumerate a new organization.

To support affiliations and enumeration of organizations, in some embodiments, the inventive computer systems match golden records just like feed entities. Matches based on fragments are similarly noted. In FIG. 11, for example, the edge between G1 and G2 denotes that the address matched at time $t_3$. Simultaneously, a claim linked the two entities via license information, denoted in the diagram as an edge between F and C2.

In some embodiments, the inventive systems include logic that processes the graph structure, examining the relationships between entities at various levels by matching entities in the feeds as well as matching between golden records. Based on the existence of paths between the vertices, and the types of paths that exist, the inventive systems can conclude that a new organization should be enumerated. In some embodiments, when the inventive systems recognize this, the inventive systems create a new organization vertex and affiliate the relevant golden record entities via edges in the graph.

In some embodiments, the graph structure described herein may be persisted in a non-relational database. In some embodiments, the inventive system can utilize TitanDB. TitanDB is a graph database that uses a column-oriented database as its storage mechanism. In such an embodiment, each vertex might be a row in a table (i.e. Column Family). Then, in some embodiments, the inventive systems of the instant invention would add a composite column for every edge, with each column containing the target vertex of the edge, the property key and property value.

In some embodiments, using a suitable non-relational model that is similar to the above described models allows the instant invention to use the native partitioning within non-relational databases to distribute the storage and processing across a set of machines. As shown, the illustrative graphs FIGS. 9-11 concisely capture the requisite information to support both intra-feed evolution as well as inter-feed processes such as consolidation, matching, group enumeration and/or affiliations. In some embodiments, the graph allows for source analysis, to determine the value and contribution of any feed. In some embodiments, a data stuard might issue a query to attain the percentage of fragment nodes for which there is a path to a golden record. In some embodiments, this would provide a good indicator as to how much value a feed contributed. Furthermore, such querying could be augmented to collect the timestamps of contribution, which would allow the data stuard to calculate the value of a feed over time.

In some embodiments, the instant invention includes one or more masterfiles that are in form of non-relational databases and/or flat files that are used as authoritative source(s) by the computer-implemented methods and the inventive computer systems of the instant invention. In some embodiments, the masterfile(s) can contain consolidated records, which contain the best information, attributes and values, available pulled from a plurality of data feeds in accordance with the principles of the instant invention as detailed herein.

In some embodiments, in pharmacy/prescription medication settings, the instant invention allows, for example (but in not limited to) to confirm, in rela-time, a prescriber eligibility to prescribe certain medications/services. In some embodiments, for example, a prescriber prescribes a medication for a patient. The patient takes the prescription to a pharmacy. A pharmacist at the pharmacy enters data into a pharmacy management system required to complete an insurance claim, for instance, using the National Council For Prescription Drug Programs ("NCPDP") standard. The pharmacists includes the prescriber's information in the claim and submits the claim to Health Management Services ("HMS") system(s). The HMS systems use the claim data in the NCPDP claim, and/or data used to build the NCPDP claim, along with HMS data to validate that the doctor/prescriber has authority to prescribe the medication/drug and that the prescriber's ID(s) that are required by federal, state, and/or local regulations are included in the NCPDP claim.

In some cases, the pharmacy, gatekeeping compliance computer software, payer(s), and/or the government may reject the claim, requiring a new prescriber and/or a resolution of the identified problem before the pharmacy is allowed to fill-in the prescription. In some cases, the pharmacy, gatekeepers (compliance coding computer software (e.g., checking Healthcare Provider Primary Taxonomy Switch(s) based on National Provider Identification (NPI) database registry)), payer(s), and/or the government may choose to override the validation process and fill the prescription. After the claim is submitted, the payer adjudicates the claim. In some embodiments, the HMS system(s) could be performing on behalf of multiple entities, including the pharmacy(ies), switch(s), payer(s), and/or government. In some embodiments, the inventive methods and systems of the instant invention compare the NCPDP claims data, and/or data used in the NCPDP claim, to HMS data to determine authority.

Figure 12:
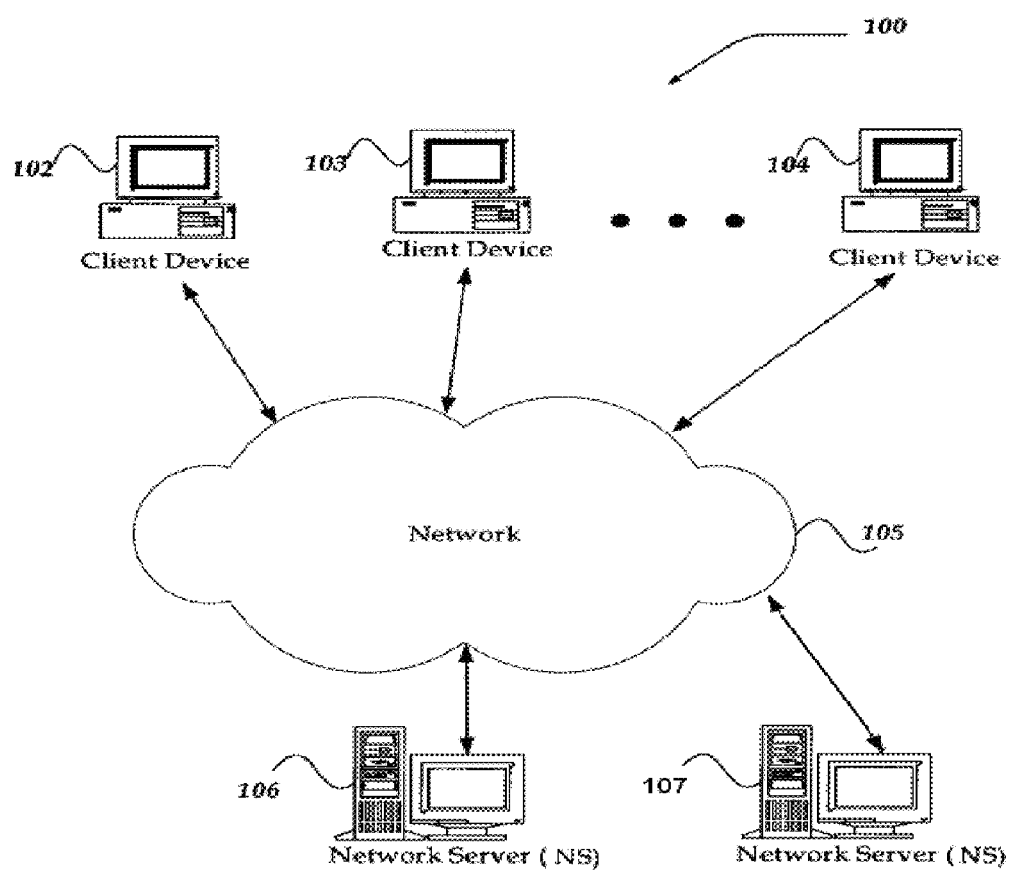
FIG. 12 illustrates a computer architecture in accordance with some embodiments of the present invention.

FIG. 12 illustrates one embodiment of an environment in which the present invention may operate. However, not all of these components may be required to practice the invention, and variations in the arrangement and type of the components may be made without departing from the spirit or scope of the invention. In some embodiment, for example, the invention computer system hosts a large number of members and concurrent transactions. In other embodiments, the invention system computer is based on a scalable computer and network architecture that incorporates varies strategies for assessing the data, caching, searching, and database connection pooling. An example of the scalable architecture is an architecture that is capable of operating multiple servers.

In some embodiments, items 102-104 in FIG. 12 represent data sources (industry databases, government agency databases, etc.)) and/or computing devices/machines of users of verified information generated/maintained by the inventive computer systems of the instant invention. In some embodiments, items 102-104 include virtually any computing device capable of receiving and sending a message over a network, such as network 105, to and from another computing device, such as servers 106 and 107, each other, and the like. In some embodiments, the set of such devices includes devices that typically connect using a wired communications medium such as personal computers, multiprocessor systems, microprocessor-based or programmable consumer electronics, network PCs, and the like. In some embodiments, the set of such devices also includes devices that typically connect using a wireless communications medium such as cell phones, smart phones, pagers, walkie talkies, radio frequency (RF) devices, infrared (IR) devices, CBs, integrated devices combining one or more of the preceding devices, or virtually any mobile device, and the like. Similarly, In some embodiments, client devices 102-104 are any device that is capable of connecting using a wired or wireless communication medium such as a PDA, POCKET PC, wearable computer, and any other device that is equipped to communicate over a wired and/or wireless communication medium.

In some embodiments, each member device within member devices 102-104 may include a browser application that is configured to receive and to send web pages, and the like. In some embodiments, the browser application may be configured to receive and display graphics, text, multimedia, and the like, employing virtually any web based language, including, but not limited to Standard Generalized Markup Language (SMGL), such as HyperText Markup Language (HTML), a wireless application protocol (WAP), a Handheld Device Markup Language (HDML), such as Wireless Markup Language (WML), WMLScript, JavaScript, and the like. In some embodiments, the systems of the instant invention are programmed in either Java or .Net.

In some embodiments, member devices 102-104 may be further configured to receive a message from the another computing device employing another mechanism, including, but not limited to email, Short Message Service (SMS), Multimedia Message Service (MMS), instant messaging (IM), internet relay chat (IRC), mIRC, Jabber, and the like. In some embodiments, network 105 may be configured to couple one computing device to another computing device to enable them to communicate. In some embodiments, network 105 may be enabled to employ any form of computer readable media for communicating information from one electronic device to another.

Also, in some embodiments, network 105 may include a wireless interface, and/or a wired interface, such as the Internet, in addition to local area networks (LANs), wide area networks (WANs), direct connections, such as through a universal serial bus (USB) port, other forms of computer-readable media, or any combination thereof. In some embodiments, on an interconnected set of LANs, including those based on differing architectures and protocols, a router may act as a link between LANs, enabling messages to be sent from one to another.

Also, in some embodiments, communication links within LANs typically include twisted wire pair or coaxial cable, while communication links between networks may utilize analog telephone lines, full or fractional dedicated digital lines including T1, T2, T3, and T4, Integrated Services Digital Networks (ISDNs), Digital Subscriber Lines (DSLs), wireless links including satellite links, or other communications links known to those skilled in the art. Furthermore, in some embodiments, remote computers and other related electronic devices could be remotely connected to either LANs or WANs via a modem and temporary telephone link. In essence, in some embodiments, network 105 includes any communication method by which information may travel between client devices 102-104, and servers 106 and 107.

In some embodiments, client devices 102-104 and servers 106 and 107 contain computer-readable media that may include, but are not limited to, an electronic, optical, magnetic, or other storage. Also, various other forms of computer-readable media may transmit or carry instructions to a computer, including a router, private or public network, or other transmission device or channel, both wired and wireless. The instructions may comprise code from any computer-programming language, including, for example, C, C++, C#, Visual Basic, Java, Python, Perl, and JavaScript.

In some examples, client devices 102-104 may be personal computers, digital assistants, personal digital assistants, cellular phones, mobile phones, smart phones, pagers, digital tablets, laptop computers, Internet appliances, and other processor-based devices.

In some embodiments, the instant invention provides for a computer-implemented method that includes at least the following steps of: electronically receiving, by at least one specialized computer system, at least ten data feeds, where each data feed contains information associated with a plurality of healthcare-related entities, where a data schema of each data feed is unknown to the at least one computer system prior to the receipt of each data feed, and where the at least one specialized computer system includes at least one specialized computer machine comprising a non-transient memory having at least one region for storing specific computer executable program code and where the at least one specialized computer machine is specifically programmed to perform at least one step of the computer-implemented method; automatically determining, by the at least one specialized computer system, in real-time, across the received data feeds, for each of the plurality of healthcare-related entities, at least the following entity information: i) at least one first type data fragment identifying at least one first identifier associated with at least one first healthcare-related entity from the plurality of healthcare-related entities; and ii) a plurality of second type data fragments, where each second type data fragment contains at least one item of information about the at least one first healthcare-related entity identified by the at least one first identifier; automatically storing, by the at least one specialized computer system, each time when the entity information for the at least one first healthcare-related entity is received, the entity information for the at least one first healthcare-related entity across a plurality of distributed non-relational computer databases, by: i) creating, for each time when the entity information for the at least one first healthcare-related entity is received, a plurality of records, where each record includes at least one first row with a plurality of columns, where the at least one first row is associated with the at least one first identifier of the at least one first healthcare-related entity from the plurality of healthcare-related entities and where each column of the at least one first row has: 1) a name composed of a hierarchical path to a content of each column, where the hierarchical path includes at least: a) a row identifier of that least one first row and b) at least one second identifier that is uniquely identifies at least one characteristic of the at the least one item of information of at least one second type data fragment, and 2) the at least one item of information of the at least one second type data fragment; or ii) updating, for each time when the entity information for the at least one first healthcare-related entity is received, the at least one first record based on: 1) determining the name of the column based on the hierarchical path, and 2) recoding the least one item of information of the at least one second type data fragment about the at least one first healthcare-related entity in a column identified by the determining the name of the column; analyzing, by the at least one specialized computer system, the plurality of distributed non-relational computer databases to determine a plurality of records associated with the at least one first healthcare-related entity; and determining, by the at least one specialized computer system, at least one first verified record of the at least one first healthcare-related entity at a particular time, where the at least one first verified record based at least in part on the entity information of the at least one first healthcare-related entity that has been stored across the plurality of distributed non-relational computer databases at each time when the entity information of the at least one first healthcare-related entity has been received.

In some embodiments, the at least one first healthcare-related entity is selected from the group of: physicians, hospitals, healthcare insurance organizations, pharmacies, healthcare industry certification authorities, and healthcare government agencies.

In some embodiments, the analyzing the plurality of distributed non-relational computer databases includes at least: creating a first plurality of relationships that tracks, over plurality of times, the entity information of the at least one first healthcare-related entity across the received data feeds; where the first plurality of relationships comprises relationships among: i) a plurality of fragment vertexes, where each fragment vertex corresponds to each second type data fragment containing the at least one item of information about the at least one first healthcare-related entity; ii) a plurality of entity vertexes, where each entity vertex corresponds to the entity information for the at least one first healthcare-related entity received at each time; and iii) a plurality of load vertexes, where each load vertex corresponds to a particular data feed with the entity information for the at least one first healthcare-related entity received at each time; and where the determining the at least one first verified record of the at least one first healthcare-related entity at the at particular time is further based on the first plurality of relationships among the plurality of fragment vertexes associated with the at least one first healthcare-related entity, the plurality of entity vertexes associated with the at least one first healthcare-related entity, and the plurality of load vertexes associated with the at least one first healthcare-related entity.

In some embodiments, the analyzing the plurality of distributed non-relational computer databases includes at least: matching the items of information about the at least one first healthcare-related entity across the plurality of fragment vertexes associated with the plurality of entity vertexes that corresponds to the at least one first healthcare-related entity, where the matching is based, at least in part, on at least one of the following: i) priority ranking among the plurality of data feeds, and ii) an age of data; and traversing the first plurality of relationships to identify at least one verified vertex that corresponds to the at least one first verified record of the at least one first healthcare-related entity at the particular time.

In some embodiments, the creating the plurality of relationships further includes at least: identifying, for each entity vertex, at least one data source, from which the entity information has been received, in the received data feeds.

In some embodiments, the analyzing the plurality of distributed non-relational computer databases further includes at least: determining a subset of the plurality of entity vertexes that are related based at least in part on matching the items of information about the at least one first healthcare-related entity across the plurality of verified vertexes; creating a second plurality of relationships to identify entities for consolidation based on the subset of the plurality of entity vertexes; and consolidating the identified entities into at least one second verified record.

In some embodiments, the analyzing the plurality of distributed non-relational computer databases further includes at least: creating at least one first organization vertex identifying at least one first organization that is related to a plurality of entities based, at least in part, on at least one first matched item of information among the plurality of fragment vertexes associated with the plurality of entity vertexes.

In some embodiments, the analyzing the plurality of distributed non-relational computer databases further includes at least: analyzing the plurality of relationships among the plurality of fragment vertexes, the plurality of entity vertexes, and plurality of load vertexes to determine that the at least one first organization is invalid; and creating at least one second organization vertex identifying at least one second organization that is related to the plurality of entities based, at least in part, on at least one second matched item of information among the plurality of fragment vertexes associated with the plurality of entity vertexes.

In some embodiments, the plurality of second type data fragments includes at least one hundred second type data fragments associated with the at least one first healthcare-related entity.

In some embodiments, the received data feeds include at least one million records related to the plurality of healthcare-related entities.

In some embodiments, the instant invention provides for a computer-implemented system that includes at least the following components/modules: at least one specialize computer machine that includes at least: a non-transient memory having at least one region for storing particular computer executable program code; and at least one processor for executing the particular program code stored in the memory, where the particular program code is configured to at least perform the following operations: electronically receiving, at least ten data feeds, where each data feed contains information associated with a plurality of healthcare-related entities, where a data schema of each data feed is unknown to the at least one computer system prior to the receipt of each data feed; automatically determining, in real-time, across the received data feeds, for each of the plurality of healthcare-related entities, at least the following entity information: i) at least one first type data fragment identifying at least one first identifier associated with at least one first healthcare-related entity from the plurality of healthcare-related entities; and ii) a plurality of second type data fragments, where each second type data fragment contains at least one item of information about the at least one first healthcare-related entity identified by the at least one first identifier; automatically storing, each time when the entity information for the at least one first healthcare-related entity is received, the entity information for the at least one first healthcare-related entity across a plurality of distributed non-relational computer databases, by: i) creating, for each time when the entity information for the at least one first healthcare-related entity is received, a plurality of records, where each record comprises at least one first row with a plurality of columns, where the at least one first row is associated with the at least one first identifier of the at least one first healthcare-related entity from the plurality of healthcare-related entities and where each column of the at least one first row has: 1) a name composed of a hierarchical path to a content of each column, where the hierarchical path comprises: a) a row identifier of that least one first row and b) at least one second identifier that is uniquely identifies at least one characteristic of the at the least one item of information of at least one second type data fragment, and 2) the at least one item of information of the at least one second type data fragment; or ii) updating, for each time when the entity information for the at least one first healthcare-related entity is received, the at least one first record based on: 1) determining the name of the column based on the hierarchical path, and 2) recoding the least one item of information of the at least one second type data fragment about the at least one first healthcare-related entity in a column identified by the determining the name of the column; analyzing, the plurality of distributed non-relational computer databases to determine a plurality of records associated with the at least one first healthcare-related entity; and determining, at least one first verified record of the at least one first healthcare-related entity at a particular time, where the at least one first verified record based at least in part on the entity information of the at least one first healthcare-related entity that has been stored across the plurality of distributed non-relational computer databases at each time when the entity information of the at least one first healthcare-related entity has been received.

Of note, the embodiments described herein may, of course, be implemented using any appropriate computer system hardware and/or computer system software. In this regard, those of ordinary skill in the art are well versed in the type of computer hardware that may be used (e.g., a mainframe, a mini-computer, a personal computer ("PC"), a network (e.g., an intranet and/or the internet)), the type of computer programming techniques that may be used (e.g., object oriented programming), and the type of computer programming languages that may be used (e.g., C++, Basic, AJAX, Javascript). The aforementioned examples are, of course, illustrative and not restrictive.

While a number of embodiments of the present invention have been described, it is understood that these embodiments are illustrative only, and not restrictive, and that many modifications may become apparent to those of ordinary skill in the art. Further still, the various steps of the above disclosed instant invention may be carried out in any desired order (and any desired steps may be added and/or any desired steps may be eliminated).

What is claimed is:

1. A computer-implemented method, comprising:
   electronically receiving, by at least one specialized computer system, during each time period of a plurality of time periods T(1) through T(n), a plurality of at least ten data feeds,
   wherein each data feed contains information associated with a plurality of healthcare-related entities,
   wherein the plurality of at least ten data feeds comprises first entity information associated with at least one first healthcare-related entity of the plurality of healthcare-related entities,
   wherein the first entity information comprises pieces of information about the at least one first healthcare-related entity, and
   wherein the at least one specialized computer system comprises at least one specialized computer machine comprising a non-transient memory having at least one region for storing specific computer executable program code and wherein the at least one specialized computer machine is specifically programmed to perform at least one step of the computer-implemented method;
   generating a plurality of layout records for the first entity information received during the plurality of time periods T(1) through T(n), wherein each layout record is associated with a timestamp corresponding to a particular time period from the plurality of time periods T(1) through T(n) and comprises:
      1) a first entity key identifier which is uniquely associated with the at least one first healthcare-related entity across a plurality of distributed non-relational computer databases, and
      2) a plurality of information identifiers, wherein each information identifier comprises:
         a) the first entity key identifier, and
         b) an information type identifier, assigned based on each type of information represented by a corresponding piece of information about the at least one first healthcare-related entity received at such particular time period;
   automatically storing, by the at least one specialized computer system, the first entity information received during the plurality of time periods T(1) through T(n) across the plurality of distributed non-relational computer databases, based, at least in part, on the plurality of layout records so that each database record of a plurality of database records for the at least one first healthcare-related entity comprises:
      i) a record identifier which is based, at least in part, on:
         1) the first entity key identifier, and
         2) the timestamp corresponding to the particular time period from the plurality of time periods T(1) through T(n),
      ii) a plurality of columns, wherein each column identifier is a hierarchical path based, at least in part, on a corresponding information identifier from the plurality of information identifiers assigned to the pieces of information about the at least one first healthcare-related entity in a particular layout record which is associated with the particular time period from the plurality of time periods T(1) through T(n);
   tracking, by the at least one specialized computer system, for each database record of the plurality of database records related to the at least one first healthcare-related entity, at least the following:
      i) a corresponding layout record from the plurality of layout records that has been utilized to store such database record,
      ii) a corresponding time period from the plurality of time periods T(1) through T(n) when the pieces of information stored in such database record have been received, and
      iii) a version data that identifies a subsequent time period from the plurality of time periods T(1) through T(n) when next pieces of information about the at least one first healthcare-related entity have been received and a subsequent layout record corresponding to the subsequent time period;
   analyzing, by the at least one specialized computer system, how the first entity information about the at least one first healthcare-related entity has changed over the plurality of time periods T(1) through T(n) based, at least in part, on the plurality of database records for the at least one first healthcare-related entity; and
   outputting, by the at least one specialized computer system, at least one first verified record of the at least one first healthcare-related entity at a particular time based, at least in part, on the analyzing how the first entity information about the at least one first healthcare-related entity has changed over the plurality of time periods T(1) through T(n).

2. The method of claim 1, wherein the at least one first healthcare-related entity is selected from the group of: physicians, hospitals, healthcare insurance organizations, pharmacies, healthcare industry certification authorities, and healthcare government agencies.

3. The method of claim 1, wherein the analyzing how the first entity information about the at least one first healthcare-related entity has changed over the plurality of time periods T(1) through T(n) comprises:
   creating a first plurality of relationships that tracks, over plurality of time periods T(1) through T(n), the first entity information of the at least one first healthcare-related entity across the received data feeds;
   wherein the first plurality of relationships comprises relationships among:
      i) a plurality of fragment vertexes, wherein each fragment vertex corresponds to each piece of information about the at least one first healthcare-related entity;
      ii) a plurality of entity vertexes, wherein each entity vertex corresponds to the first entity information for the at least one first healthcare-related entity received at each time of the plurality of time periods T(1) through T(n); and iii) a plurality of load vertexes, wherein each load vertex corresponds to a particular data feed with the first entity information for the at least one first healthcare-related entity received at each time of the plurality of time periods T(1) through T(n); and wherein the outputting the at least one first verified record of the at least one first healthcare-related entity at the particular time is further based on the first plurality of relationships among the plurality of fragment vertexes associated with the at least one first healthcare-related entity, the plurality of entity vertexes associated with the at least one first healthcare-related entity, and the plurality of load vertexes associated with the at least one first healthcare-related entity.

4. The method of claim 3, wherein the analyzing how the first entity information about the at least one first healthcare-related entity has changed over the plurality of time periods T(1) through T(n) comprises:

matching the pieces of information about the at least one first healthcare-related entity across the plurality of fragment vertexes associated with the plurality of entity vertexes that correspond to the at least one first healthcare-related entity, wherein the matching is based, at least in part, on at least one of the following:
i) priority ranking among the plurality of data feeds, and
ii) an age of data; and traversing the first plurality of relationships to identify at least one verified vertex that corresponds to the at least one first verified record of the at least one first healthcare-related entity at the particular time.

5. The method of claim 3, wherein the creating the plurality of relationships further comprises:

identifying, for each entity vertex, at least one data source, from which the entity information has been received, in the received data feeds.

6. The method of claim 4, wherein the analyzing how the first entity information about the at least one first healthcare-related entity has changed over the plurality of time periods T(1) through T(n) further comprises:

determining a subset of the plurality of entity vertexes that are related based at least in part on matching the pieces of information about the at least one first healthcare-related entity across the plurality of verified vertexes;

creating a second plurality of relationships to identify entities for consolidation based on the subset of the plurality of entity vertexes; and consolidating the identified entities into at least one second verified record.

7. The method of claim 6, wherein the analyzing how the first entity information about the at least one first healthcare-related entity has changed over the plurality of time periods T(1) through T(n) further comprises:

creating at least one first organization vertex identifying at least one first organization that is related to a plurality of entities based, at least in part, on at least one first matched piece of information among the plurality of fragment vertexes associated with the plurality of entity vertexes.

8. The method of claim 7, wherein the analyzing how the first entity information about the at least one first healthcare-related entity has changed over the plurality of time periods T(1) through T(n) further comprises:

analyzing the plurality of relationships among the plurality of fragment vertexes, the plurality of entity vertexes, and plurality of load vertexes to determine that the at least one first organization is invalid; and creating at least one second organization vertex identifying at least one second organization that is related to the plurality of entities based, at least in part, on at least one second matched piece of information among the plurality of fragment vertexes associated with the plurality of entity vertexes.

9. The method of claim 1, wherein the plurality of pieces of information comprises at least one hundred pieces of information associated with the at least one first healthcare-related entity.

10. The method of claim 1, wherein the received data feeds comprise at least one million records related to the plurality of healthcare-related entities.

11. The method of claim 1, wherein a data schema of each data feed is unknown to the at least one computer system prior to the receipt of such data feed.

12. A computer system, comprising:
at least one specialize computer machine, comprising:
a non-transient memory having at least one region for storing particular computer executable program code; and
at least one processor for executing the particular program code stored in the memory, wherein the particular program code is configured to at least perform the following operations:
electronically receiving, during each time period of a plurality of time periods T(1) through T(n), a plurality of at least ten data feeds,
wherein each data feed contains information associated with a plurality of healthcare-related entities,
wherein the plurality of at least ten data feeds comprises first entity information associated with at least one first healthcare-related entity of the plurality of healthcare-related entities, and
wherein the first entity information comprises pieces of information about the at least one first healthcare-related entity;
generating a plurality of layout records for the first entity information received during the plurality of time periods T(1) through T(n), wherein each layout record is associated with a timestamp corresponding to a particular time period from the plurality of time periods T(1) through T(n) and comprises:
1) a first entity key identifier which is uniquely associated with the at least one first healthcare-related entity across a plurality of distributed non-relational computer databases, and
2) a plurality of information identifiers, wherein each information identifier comprises:
a) the first entity key identifier, and
b) an information type identifier, assigned based on each type of information represented by a corresponding piece of information about the at least one first healthcare-related entity received at such particular time period;
automatically storing, the first entity information received during the plurality of time periods T(1) through T(n) across the plurality of distributed non-relational computer databases, based, at least in part, on the plurality of layout records so that each database record of a plurality of database records for the at least one first healthcare-related entity comprises:

i) a record identifier which is based, at least in part, on:
   1) the first entity key identifier, and
   2) the timestamp corresponding to the particular time period from the plurality of time periods T(1) through T(n),
ii) a plurality of columns, wherein each column identifier is a hierarchical path based, at least in part, on a corresponding information identifier from the plurality of information identifiers assigned to the pieces of information about the at least one first healthcare-related entity in a particular layout record which is associated with the particular time period from the plurality of time periods T(1) through T(n);

tracking, for each database record of the plurality of database records related to the at least one first healthcare-related entity, at least the following:
   i) a corresponding layout record from the plurality of layout records that has been utilized to store such database record,
   ii) a corresponding time period from the plurality of time periods T(1) through T(n) when the pieces of information stored in such database record have been received, and
   iii) a version data that identifies a subsequent time period from the plurality of time periods T(1) through T(n) when next pieces of information about the at least one first healthcare-related entity have been received and a subsequent layout record corresponding to the subsequent time period;

analyzing how the first entity information about the at least one first healthcare-related entity has changed over the plurality of time periods T(1) through T(n) based, at least in part, on the plurality of database records for the at least one first healthcare-related entity; and outputting at least one first verified record of the at least one first healthcare-related entity at a particular time based, at least in part, on the analyzing how the first entity information about the at least one first healthcare-related entity has changed over the plurality of time periods T(1) through T(n).

13. The system of claim 12, wherein the at least one first healthcare-related entity is selected from the group of: physicians, hospitals, healthcare insurance organizations, pharmacies, healthcare industry certification authorities, and healthcare government agencies.

14. The system of claim 12, wherein the analyzing how the first entity information about the at least one first healthcare-related entity has changed over the plurality of time periods T(1) through T(n) comprises:
   creating a first plurality of relationships that tracks, over plurality of time periods T(1) through T(n), the first entity information of the at least one first healthcare-related entity across the received data feeds;
   wherein the first plurality of relationships comprises relationships among:
      i) a plurality of fragment vertexes, wherein each fragment vertex corresponds to each piece of information second type data fragment containing the at least one item of information about the at least one first healthcare-related entity;
      ii) a plurality of entity vertexes, wherein each entity vertex corresponds to the first entity information for the at least one first healthcare-related entity received at each time of the plurality of time periods T(1) through T(n); and
      iii) a plurality of load vertexes, wherein each load vertex corresponds to a particular data feed with the first entity information for the at least one first healthcare-related entity received at each time of the plurality of time periods T(1) through T(n); and
   wherein the outputting the at least one first verified record of the at least one first healthcare-related entity at the particular time is further based on the first plurality of relationships among the plurality of fragment vertexes associated with the at least one first healthcare-related entity, the plurality of entity vertexes associated with the at least one first healthcare-related entity, and the plurality of load vertexes associated with the at least one first healthcare-related entity.

15. The system of claim 14, wherein the analyzing how the first entity information about the at least one first healthcare-related entity has changed over the plurality of time periods T(1) through T(n) comprises:
   matching the pieces of information about the at least one first healthcare-related entity across the plurality of fragment vertexes associated with the plurality of entity vertexes that correspond to the at least one first healthcare-related entity, wherein the matching is based, at least in part, on at least one of the following:
      i) priority ranking among the plurality of data feeds, and
      ii) an age of data; and
   traversing the first plurality of relationships to identify at least one verified vertex that corresponds to the at least one first verified record of the at least one first healthcare-related entity at the particular time.

16. The system of claim 14, wherein the creating the plurality of relationships further comprises:
   identifying, for each entity vertex, at least one data source, from which the entity information has been received, in the received data feeds.

17. The system of claim 13, wherein the analyzing how the first entity information about the at least one first healthcare-related entity has changed over the plurality of time periods T(1) through T(n) further comprises:
   determining a subset of the plurality of entity vertexes that are related based at least in part on matching the pieces of information about the at least one first healthcare-related entity across the plurality of verified vertexes;
   creating a second plurality of relationships to identify entities for consolidation based on the subset of the plurality of entity vertexes; and
   consolidating the identified entities into at least one second verified record.

18. The system of claim 17, wherein the analyzing how the first entity information about the at least one first healthcare-related entity has changed over the plurality of time periods T(1) through T(n) further comprises:
   creating at least one first organization vertex identifying at least one first organization that is related to a plurality of entities based, at least in part, on at least one first matched piece of information among the plurality of fragment vertexes associated with the plurality of entity vertexes.

19. The system of claim 18, wherein the analyzing how the first entity information about the at least one first healthcare-related entity has changed over the plurality of time periods T(1) through T(n) further comprises:
   analyzing the plurality of relationships among the plurality of fragment vertexes, the plurality of entity vertexes, and plurality of load vertexes to determine that the at least one first organization is invalid; and
   creating at least one second organization vertex identifying at least one second organization that is related to the plurality of entities based, at least in part, on at least one second matched piece of information among the plurality of fragment vertexes associated with the plurality of entity vertexes.

20. The system of claim 12, wherein the plurality of pieces of information comprises at least one hundred pieces of information associated with the at least one first healthcare-related entity.

21. The system of claim 12, wherein the received data feeds comprise at least one million records related to the plurality of healthcare-related entities.

22. The system of claim 12, wherein a data schema of each data feed is unknown to the at least one computer system prior to the receipt of such data feed.

* * * * *